United States Patent
Mauriac et al.

(10) Patent No.: US 8,206,621 B2
(45) Date of Patent: Jun. 26, 2012

(54) USE OF ETHANOL AS PLASTICIZER FOR PREPARING SUBCUTANEOUS IMPLANTS CONTAINING THERMOLABILE ACTIVE PRINCIPLES DISPERSED IN A PLGA MATRIX

(75) Inventors: Patrice Mauriac, Paris (FR); Pierre Marion, Neuilly Plaisance (FR)

(73) Assignee: Mediolanum Pharmaceuticals Ltd., Dublin (IE)

( * ) Notice: Subject to any disclaimer, the term of this patent is extended or adjusted under 35 U.S.C. 154(b) by 1493 days.

(21) Appl. No.: 10/562,707

(22) PCT Filed: Jun. 24, 2004

(86) PCT No.: PCT/EP2004/051226
§ 371 (c)(1),
(2), (4) Date: Dec. 23, 2005

(87) PCT Pub. No.: WO2005/000277
PCT Pub. Date: Jan. 6, 2005

(65) Prior Publication Data
US 2006/0171987 A1    Aug. 3, 2006

(30) Foreign Application Priority Data
Jun. 26, 2003 (IT) .............................. MI2003A1302

(51) Int. Cl.
*B01J 13/02* (2006.01)
*B01J 13/18* (2006.01)
*A61K 9/127* (2006.01)
(52) U.S. Cl. .......................... 264/4.6; 264/4.3; 264/4.33
(58) Field of Classification Search ........................ None
See application file for complete search history.

(56) References Cited

U.S. PATENT DOCUMENTS
5,520,923 A    5/1996    Northey et al.

FOREIGN PATENT DOCUMENTS
| WO | WO0033809 | 6/2000 |
| WO | WO03041685 | 5/2003 |

*Primary Examiner* — Carlos Azpuru
(74) *Attorney, Agent, or Firm* — Abelman, Frayne & Schwab

(57) ABSTRACT

A plasticized polymer of PLGA employing ethanol as the plasticizing agent prepared at a temperature higher than the Tg and lower than the boiling point of ethanol can be used in subcutaneous implants containing active ingredients therein.

17 Claims, No Drawings

USE OF ETHANOL AS PLASTICIZER FOR PREPARING SUBCUTANEOUS IMPLANTS CONTAINING THERMOLABILE ACTIVE PRINCIPLES DISPERSED IN A PLGA MATRIX

FIELD OF THE INVENTION

The present invention relates to the use of ethanol as plasticizer for preparing subcutaneous implants containing thermolabile active principles dispersed in a PLGA matrix.

STATE OF THE ART

In the current state of the art the extrusion temperature of PLGA is higher than 75° C. Typically the temperature during extrusion must be 40-50° C. above the Tg of the polymer to be extruded.

With this type of technique it is not possible to prepare subcutaneous implants containing a thermolabile active principle dispersed in a polylactic-glycolic acid (PLGA) matrix.

To use such a technique to prepare subcutaneous implants with active principles of this type, the extrusion temperature must be lowered. In general to lower the extrusion temperature the use of a plasticizer is widespread which allows the flexibility and the workability of the polymer to be increased following the reduction of the Tg thereof. The amount of plasticizer to be added to the polymer varies as a function of the desired effect.

An essential requirement for a plasticizer is non-volatility. Currently modern plasticizers are organic synthetic compounds; in most cases they are esters such as adipates and phthalates. These types of products are not biocompatible and therefore cannot be used for subcutaneous implants for application to man and to mammals in general.

For other types of plasticizers such as triacetin, N-methyl-2-pyrrolidone, glycerol and formaldehyde, their toxicity to man and to mammals has not been fully ascertained.

In preparing said type of subcutaneous implants the requirement was therefore felt for a plasticizer able to reduce the extrusion temperature of PLGA which did not present the drawbacks of the state of the art and was non-toxic.

SUMMARY OF THE INVENTION

In particular the Applicant has found that ethanol while being a volatile substance diffuses rapidly and in a homogeneous manner in ground PLGA at a temperature higher than the Tg and lower than the boiling point of ethanol and therefore subcutaneous implants using ethanol as external plasticizing agent can be prepared.

The term "external plasticizer" means a plasticizing agent to be used in the process of preparing the subcutaneous implant by extrusion, but in a phase previous to the aforesaid preparation, or rather in the preparation phase of the "plasticized" polymer which will be subsequently used in the preparation of the subcutaneous implant.

A further aspect of the present invention is therefore a plasticized PLGA containing ethanol as plasticizing agent.

This plasticized polymer is therefore prepared using a process which comprises the following stages:

a) grinding PLGA to obtain a ground product in which the particles have dimensions less than 250 µm;
b) adding ethanol to the ground product obtained in the preceding stage in concentrations between 5 and 20 parts by weight/weight of PLGA and then heating the mixture obtained to a temperature between 45 and 65° C., until a viscous and stable gel is obtained;
c) drying the gel obtained in step (b)
d) grinding the dried product coming from step (c) at a temperature between −20 and +5° C.;
e) optionally mixing the product originating from the preceding stage with PLGA as such which has been previously ground until a ground product of dimensions less than 250 µm is obtained, in weight ratios between 10:90 and 99:1 respectively, at a temperature between −20 and +5° C.;
f) extruding the aforesaid mixture at 75° C.;
g) grinding the extruded product at a temperature between −20° C. and +5° C. to obtain the PLGA plasticized with ethanol according to the present invention.

A further aspect of the present invention is a subcutaneous implant comprising an active principle dispersed in a matrix based on PLGA plasticized with ethanol according to the present invention.

DETAILED DESCRIPTION OF THE INVENTION

The plasticized PLGA of the present invention generally contains ethanol in concentrations between 2 and 15%, preferably between 3 and 10%, and even more preferably between 5 and 10% by weight on the weight of PLGA.

The Applicant has in fact found that by using plasticized PLGA containing ethanol at concentrations between 2% and 3% by weight, the Tg of the polymer and consequently the extrusion temperature can be reduced to temperatures lower than 70° C.; by using ethanol at concentrations higher than between 3 and 4% by weight, this temperature can be reduced to values lower than 60° C.

The Applicant has also found that using ethanol at concentrations between 5 and 10% on the weight of plasticized polymer, the extrusion temperature can be reduced to 40° C. (i.e. a temperature compatible with most thermolabile biological active principles).

The plasticized polymer according to the present invention therefore contains ethanol in concentrations preferably between 5 and 10%, when used for preparing compositions for subcutaneous implants containing thermolabile active principles. Preferably in stage (b) the amount of ethanol added is equal to 10 parts by weight per parts by weight of PLGA.

In stage (c) drying is conducted until obtaining a concentration of ethanol in PLGA preferably comprised between 10 and 30%, more preferably 20% by weight/PLGA weight. Preferably drying in step (c) is carried out under an air stream at a temperature comprised between 20 and 25° C.

The temperature of grinding in stage (d), (e) and (g) is preferably −10° C., while in stage (e) the weight ratio of PLGA originating from stage (d)/PLGA as such is preferably between 16:84 and 40:60.

By increasing in stage (e) the concentration by weight of PLGA treated with ethanol with respect to the untreated PLGA, the extrusion temperature of the subsequent subcutaneous implant preparation phase is reduced.

The subcutaneous implants, a further aspect of the present invention, are prepared by a process comprising the following stages:

i) mixing the active principle with the plasticized PLGA of the present invention, at a temperature between −20° C. and +5° C.
ii) extruding the ground product originating from stage (i) at a temperature less than 70° C., preferably less than 60° C.

As stated above, when the plasticized polymer used in stage (i) contains between 5 and 10% of ethanol, the extrusion temperature in stage (ii) is about 40° C.

In this case the aforesaid process is particularly suitable for preparing subcutaneous implants comprising thermolabile active principles. The term "thermolabile active principles" means active principles which must be stored at low temperature and in particular proteins (hormones, growth factors, enzymes etc), vaccines, antibodies and vectors for genic therapy.

The polymer plasticized with ethanol according to the present invention can also be used for preparing subcutaneous implants containing non-thermolabile active principles, however in any event as a precaution it is preferable not to subject them to sudden temperature changes.

Some illustrative but non-limitative examples of the preparation of plasticized polymer containing ethanol of the present invention together with the preparation of the subcutaneous implant of the present invention containing PLGA plasticized with ethanol and containing a thermolabile active principle are reported herein below.

EXAMPLE 1

Preparation of Subcutaneous Implants Containing Recombinant Human Granulocyte Colony Stimulating Factor (r-Hu-G-CSF)

a) Preparation of PLGA Plasticized with Ethanol
PLGA having the following characteristics:
inherent viscosity 0.19 dl/g measured at 25° C. in chloroform (c=0.1 g/dl),
Lactide/Glycolide Molar ratio: 53/47,
Tg: 40° C.

The ground product is added to an excess of ethanol until a concentration of PLGA in ethanol equal to 0.12 g/ml is obtained and is placed in a bath of water heated to 45° C. and stirred for 1 minute. The ethanol diffuses into the polymer and forms a viscous gel. This gel is maintained in ethanol for 3 minutes.

This is followed by drying at 20° C. until a PLGA is obtained containing ethanol in a quantity equal to 20% weight/weight.

The polymer thus obtained is mixed at −10° C. with the same untreated type of polymer as such in a weight ratio of 40:60 and the said mixture is then extruded at 75° C.

The extruded product is then ground at −10° C. to obtain the plasticized PLGA with an ethanol content of 8% mass/mass.

b) Preparation of the Subcutaneous Implant
The active principle consisting of the protein r-Hu-G-CSF having the following characteristics:
Protein content (Colorimetry—Bradford): 2.1 to 2.6% mass/mass,
Biological potency (In vitro—Std WHO #88/502): 21 to $31 \times 10^6$ IU/mg of protein,
Excipients:
Mannitol/Polysorbate 80/Sodium Phosphate monobasic/Sodium Phosphate Dibasic Dodecahydrated/Human Albumin (93.4%/0.01%/1.9%/0.5%/1.9% mass/mass respectively)
and the plasticized polymer (PLGA) were mixed intimately at −10° C. in a weight ratio of 31:69 respectively.

The powdered mixture thus obtained was extruded at 40° C. The extruded product thus obtained (1.5 mm in diameter) was then cut to a length of 18 mm to form cylindrical deposits each weighing 40 mg and each containing the protein in a quantity equal to $6.6 \times 10^6$ IU.

EXAMPLE 2

Preparation of Subcutaneous Implants Containing Recombinant Human Granulocyte Colony Stimulating Factor (r-Hu-G-CSF)

a) Preparation of PLGA Plasticized with Ethanol
PLGA having the same characteristics as the one described in the Example 1 is ground until a particle size of less than 250 μm is obtained.

The ground product is added to an excess of ethanol until a concentration of PLGA in ethanol equal to 0.12 g/ml is obtained and is placed in a bath of water heated to 45° C. and stirred for 1 minute. The ethanol diffuses into the polymer and forms a viscous gel. This gel is maintained in ethanol for 3 minutes.

This is followed by drying at 20° C. until a PLGA is obtained containing ethanol in a quantity equal to 20% weight/weight.

The polymer thus obtained is mixed at −10° C. with the same untreated type of polymer as such in a weight ratio of 32.5:67.5 and the said mixture is then extruded at 75° C.

The extruded product is then ground at −10° C. to obtain the plasticized PLGA with an ethanol content of 6.5% mass/mass.

b) Preparation of the Subcutaneous Implant
The active principle consisting of the protein r-Hu-G-CSF having the same characteristics that the one described in the Example 1 and the plasticized polymer (PLGA) were mixed intimately at −10° C. in a weight ratio of 30:70 respectively.

The powdered mixture thus obtained was extruded at 50° C. The extruded product thus obtained (1.5 mm in diameter) was then cut to a length of 18 mm to form cylindrical deposits each weighing 40 mg and each containing the protein in a quantity equal to $6.6 \times 10^6$ IU.

EXAMPLE 3

Preparation of Subcutaneous Implants Containing Recombinant Human Granulocyte Colony Stimulating Factor (r-Hu-G-CSF)

a) Preparation of PLGA Plasticized with Ethanol
PLGA having the same characteristics as the one described in the Example 1 is ground until a particle size of less than 250 μm is obtained.

The ground product is added to an excess of ethanol until a concentration of PLGA in ethanol equal to 0.12 g/ml is obtained and is placed in a bath of water heated to 45° C. and stirred for 1 minute. The ethanol diffuses into the polymer and forms a viscous gel. This gel is maintained in ethanol for 3 minutes.

This is followed by drying at 20° C. until a PLGA is obtained containing ethanol in a quantity equal to 20% mass/mass.

The polymer thus obtained is mixed at −10° C. with the same untreated type of polymer as such in a weight ratio of 16:84 and the said mixture is then extruded at 75° C.

The extruded product is then ground at −10° C. to obtain the plasticized PLGA with an ethanol content of 3.2% mass/mass.

b) Preparation of the Subcutaneous Implant

The active principle consisting of the protein r-Hu-G-CSF having the same characteristics as the one described in the Example 1 and the plasticized polymer (PLGA) were mixed intimately at −10° C. in a weight ratio of 30:70 respectively.

The powdered mixture thus obtained was extruded at 60° C. The extruded product thus obtained (1.5 mm in diameter) was then cut to a length of 18 mm to form cylindrical deposits each weighing 40 mg and each containing the protein in a quantity equal to $6.6 \times 10^6$ IU.

EXAMPLE 4

Preparation of Subcutaneous Implants Containing Recombinant Human Growth Hormone (r-Hu-GH)

a) Preparation of PLGA Plasticized with Ethanol

PLGA having the following characteristics is ground until a particle size of less than 250 μm is obtained.
 inherent viscosity 0.19 dl/g measured at 25° C. in chloroform (c=0.1 g/dl),
 Lactide/Glycolide Molar ratio: 53/47,
 Tg: 40° C.

The ground product is added to an excess of ethanol until a concentration of PLGA in ethanol equal to 0.12 g/ml is obtained and is placed in a bath of water heated to 45° C. and stirred for 1 minute. The ethanol diffuses into the polymer and forms a viscous gel. This gel is maintained in ethanol for 3 minutes.

This is followed by drying at 20° C. until a PLGA is obtained containing ethanol in a quantity equal to 20% mass/mass.

The polymer thus obtained is mixed at −10° C. with the same untreated type of polymer as such in a weight ratio of 40:60, and the said mixture is then extruded at 75° C.

The extruded product is then ground at −10° C. to obtain the plasticized PLGA with an ethanol content of 8% mass/mass.

b) Preparation of the Subcutaneous Implant

The active principle consisting of the protein r-Hu-GH having the following characteristics:
 Related proteins (Liquid Chromatography according to the monograph "Somatropin"—Nr 0951 of the 4th Edition of the European Pharmacopoeia): maximum 13% (peaks area),
 Dimer and related substances of higher molecular mass (Size Exclusion Chromatography according to the monograph "Somatropin"—Nr 0951 of the 4th Edition of the European Pharmacopoeia): maximum 6% (peaks area),
 Protein Content (Size Exclusion Chromatography according to the monograph "Somatropin"—Nr 0951 of the 4th Edition of the European Pharmacopoeia): 4.5 to 5.3% mass/mass,
 Biological potency (Size Exclusion Chromatography according to the monograph "Somatropin"—Nr 0951 of the 4th Edition of the European Pharmacopoeia): 2.7 to 3.2 IU/mg of protein,
 Excipients:
Glycin/Sodium Phosphate monobasic/Sodium Phosphate Dibasic Dodecahydrated
(91.4%/1.0%/2.5% mass/mass respectively)
and the plasticized polymer (PLGA) were mixed intimately at −10° C. in a weight ratio of 30:70 respectively.

The powdered mixture thus obtained was extruded at 40° C. The extruded product thus obtained (1.5 mm in diameter) was then cut to a length of 18 mm to form cylindrical deposits each weighing 40 mg and each containing the protein in a quantity equal to 1.8 IU.

The integrity of the protein within the depots was examined through the following analytical package:
 Related proteins by Liquid Chromatography according to the monograph "Somatropin" (Nr 0951) of the 4th Edition of the European Pharmacopoeia,
 Dimer and related substances of higher molecular mass by Size Exclusion Chromatography according to the monograph "Somatropin" (Nr 0951) of the 4th Edition of the European Pharmacopoeia,
 Assay by Size Exclusion Chromatography according to the monograph "Somatropin" (Nr 0951) of the 4th Edition of the European Pharmacopoeia.

EXAMPLE 5

Preparation of Subcutaneous Implants Containing Recombinant Human Growth Hormone (r-Hu-GH)

a) Preparation of PLGA Plasticized with Ethanol

PLGA having the same characteristics as the one described in the Example 4 is ground until a particle size of less than 250 μm is obtained.

The ground product is added to an excess of ethanol until a concentration of PLGA in ethanol equal to 0.12 g/ml is obtained and is placed in a bath of water heated to 45° C. and stirred for 1 minute. The ethanol diffuses into the polymer and forms a viscous gel. This gel is maintained in ethanol for 3 minutes.

This is followed by drying at 20° C. until a PLGA is obtained containing ethanol in a quantity equal to 20% mass/mass.

The polymer thus obtained is mixed at −10° C. with the same untreated type of polymer as such in a weight ratio of 32.5:67.5 and the said mixture is then extruded at 75° C.

The extruded product is then ground at −10° C. to obtain the plasticized PLGA with an ethanol content of 6.5% mass/mass.

b) Preparation of the Subcutaneous Implant

The active principle consisting of the protein r-Hu-GH having the same characteristics as the one described in the Example 4 and the plasticized polymer (PLGA) were mixed intimately at −10° C. in a weight ratio of 30:70 respectively.

The powdered mixture thus obtained was extruded at 50° C. The extruded product thus obtained (1.5 mm in diameter) was then cut to a length of 18 mm to form cylindrical deposits each weighing 40 mg and each containing the protein in a quantity equal to 1.8 IU.

The integrity of the protein within the depots was examined through the same analytical package that the one described for Example 4.

EXAMPLE 6

Preparation of Subcutaneous Implants Containing Recombinant Human Growth Hormone (r-Hu-GH)

a) Preparation of PLGA Plasticized with Ethanol

PLGA having the same characteristics as the one described in the Example 4 is ground until a particle size of less than 250 μm is obtained.

The ground product is added to an excess of ethanol until a concentration of PLGA in ethanol equal to 0.12 g/ml is obtained and is placed in a bath of water heated to 45° C. and stirred for 1 minute. The ethanol diffuses into the polymer and forms a viscous gel. This gel is maintained in ethanol for 3 minutes.

This is followed by drying at 20° C. until a PLGA is obtained containing ethanol in a quantity equal to 20% mass/mass.

The polymer thus obtained is mixed at −10° C. with the same untreated type of polymer as such in a weight ratio of 16:84 and the said mixture is then extruded at 75° C.

The extruded product is then ground at −10° C. to obtain the plasticized PLGA with an ethanol content of 3.2% mass/mass.

b) Preparation of the Subcutaneous Implant

The active principle consisting of the protein r-Hu-G-CSF having the same characteristics as the one described in the Example 4 and the plasticized polymer (PLGA) were mixed intimately at −10° C. in a weight ratio of 30:70 respectively.

The powdered mixture thus obtained was extruded at 60° C. The extruded product thus obtained (1.5 mm in diameter) was then cut to a length of 18 mm to form cylindrical deposits each weighing 40 mg and each containing the protein in a quantity equal to 1.8 IU.

EXAMPLE 7

Preparation of Subcutaneous Implants Containing Interferon Alfa-2a a) Preparation of PLGA Plasticized with Ethanol PLGA having the following characteristics is ground until a particle size of less than 250 μm is obtained.
inherent viscosity 0.19 dl/g measured at 25° C. in chloroform (c=0.1 g/dl),
Lactide/Glycolide Molar ratio: 53/47,
Tg: 40° C.

The ground product is added to an excess of ethanol until a concentration of PLGA in ethanol equal to 0.12 g/ml is obtained and is placed in a bath of water heated to 45° C. and stirred for 1 minute. The ethanol diffuses into the polymer and forms a viscous gel. This gel is maintained in ethanol for 3 minutes.

This is followed by drying at 20° C. until a PLGA is obtained containing ethanol in a quantity equal to 20% mass/mass.

The polymer thus obtained is mixed at −10° C. with the same untreated type of polymer as such in a weight ratio of 40:60 and the said mixture is then extruded at 75° C.

The extruded product is then ground at −10° C. to obtain the plasticized PLGA with an ethanol content of 8% mass/mass.

b) Preparation of the Subcutaneous Implant

The active principle consisting of the protein Interferon alfa-2a having the following characteristics:
Related proteins (Liquid Chromatography according to the monograph "Interferon alfa-2 Concentrated solution"— Nr 1110 of the 4th Edition of the European Pharmacopoeia): maximum 5% (peaks area),
Protein Content: 1.8% mass/mass,
Biological potency (Size Exclusion Chromatography according to the monograph "Interferon alfa-2 Concentrated solution"—Nr 1110 of the 4th Edition of the European Pharmacopoeia): $2.3 \times 10^8$ IU/mg of protein,
Excipients:
Sodium Acetate/Sodium Chloride/Trehalose (5.9%/8.4%/83.9% mass/mass respectively)
and the plasticized polymer (PLGA) were mixed intimately at −10° C. in a weight ratio of 25:75 respectively.

The powdered mixture thus obtained was extruded at 40° C. The extruded product thus obtained (1.5 mm in diameter) was then cut to a length of 18 mm to form cylindrical deposits each weighing 40 mg and each containing the protein in a quantity equal to $40 \times 10^6$ IU.

The integrity of the protein within the depots was examined through the following analytical package:
Related proteins by Liquid Chromatography according to the monograph "Interferon alfa-2 Concentrated solution" (Nr 1110) of the 4th Edition of the European Pharmacopoeia.

The invention claimed is:

1. PLGA plasticized with ethanol, obtained by a process comprising the following steps:
   a) grinding PLGA to obtain a ground product in which the particles have dimensions less than 250 μm;
   b) adding ethanol to the ground product obtained in the preceding step in concentrations between 5 and 20 parts by weight/weight of PLGA and heating the mixture obtained to a temperature between 45 and 65° C., until a viscous and stable gel is obtained;
   c) drying the product coming from step (b),
   d) grinding the dried product obtained at a temperature ranging from −20 and +5° C.;
   f) extruding the aforesaid product at 75° C., and
   g) grinding the extruded product at a temperature between −20° C. and +5° C.,
   said process optionally comprising a step e), to be performed before step f), of mixing the product coming from step d) with untreated PLGA, which has been previously ground until a ground product of particle size less than 250 μm is obtained, in a weight ratio of product coming from step d)/untreated PLGA between 10:90 and 99:1, at a temperature between −20 and +5° C.

2. Plasticized PLGA as claimed in claim 1 containing ethanol in concentrations between 2 and 15% by weight on the weight of PLGA.

3. Plasticized PLGA as claimed in claim 2 wherein said ethanol concentrations are between 3 and 10% by weight on the weight of PLGA.

4. Plasticized PLGA as claimed in claim 2 wherein said concentrations are between 5 and 10% by weight on the weight of PLGA.

5. Plasticised PLGA according to claim 1, wherein in step (b) the ethanol is added in a quantity of 10 parts by weight/weight of PLGA.

6. Plasticised PLGA according to claim 1, wherein in step (d) the drying is conducted until obtaining an ethanol concentration in PLGA between 10 and 30%/by weight/PLGA weight.

7. Plasticised PLGA according to claim 6 wherein said ethanol concentration is 20% by weight/PLGA weight.

8. Plasticised PLGA according to claim 6, wherein said drying is carried out at a temperature between 20 and 25° C. under an air stream.

9. Plasticised PLGA as claimed in claim 1, wherein the grinding temperature in step (d), (e) and (g) is −10° C.

10. Plasticised PLGA as claimed in claim 1 wherein in step (e) the weight ratio of PLGA coming from step (d)/untreated PLGA is between 16:84 and 40:60.

11. Subcutaneous implants obtained by extrusion, containing an active principle dispersed in PLGA plasticized with ethanol as claimed in claim 1.

12. Subcutaneous implants as claimed in claim 11 containing thermolabile active principles.

13. Subcutaneous implants as claimed in claim 12, wherein said thermolabile active principles are selected from the group consisting of proteins, vaccines, antibodies and vectors for genic therapy.

14. A process for preparing a subcutaneous implant obtained by extrusion containing an active principle dispersed in PLGA plasticized with ethanol according to claim 1, comprising the following steps:
   i) mixing the active principle with the plasticized PLGA as claimed in claim 1, at a temperature between −20° C. and +5° C.,
   ii) extruding the ground product originating from step (i) at a temperature less than 70° C.

15. The process as claimed in claim 14, wherein the temperature of step (i) is −10° C.

16. The process as claimed in claim 14 wherein the temperature of step (ii) is less than 60° C. when plasticized PLGA containing when plasticized PLGA containing ethanol at concentrations between 3 and 4% by weight on the weight of PLGA is used in step (i).

17. The process as claimed in claim 15, wherein the temperature of step (ii) is equal to 40° C., when plasticized PLGA containing ethanol at concentrations between 5 and 10% by weight/weight of PLGA is used.

* * * * *